United States Patent
Clark et al.

(10) Patent No.: US 9,476,831 B2
(45) Date of Patent: Oct. 25, 2016

(54) ALKYLAROMATICS PRODUCTION USING DILUTE ALKENE

(75) Inventors: Michael C. Clark, Chantilly, VA (US); Brian Maerz, Chelmsford, MA (US)

(73) Assignee: BADGER LICENSING LLC, Boston, MA (US)

( * ) Notice: Subject to any disclaimer, the term of this patent is extended or adjusted under 35 U.S.C. 154(b) by 654 days.

(21) Appl. No.: 13/042,004

(22) Filed: Mar. 7, 2011

(65) Prior Publication Data
US 2011/0160506 A1    Jun. 30, 2011

Related U.S. Application Data

(63) Continuation of application No. 11/886,046, filed as application No. PCT/US2006/007262 on Mar. 1, 2006, now Pat. No. 7,923,589.

(60) Provisional application No. 60/666,809, filed on Mar. 31, 2005.

(51) Int. Cl.
| | | |
|---|---|---|
| C07C 2/66 | (2006.01) | |
| C07C 6/12 | (2006.01) | |
| G01N 21/64 | (2006.01) | |
| C07C 2/64 | (2006.01) | |
| A61B 5/083 | (2006.01) | |

(52) U.S. Cl.
CPC ............. *G01N 21/643* (2013.01); *C07C 2/64* (2013.01); *C07C 6/12* (2013.01); *A61B 5/0833* (2013.01)

(58) Field of Classification Search
CPC .................................. C07C 2/66; C07C 6/12
USPC ................................ 585/449, 323, 475, 467
See application file for complete search history.

(56) References Cited

U.S. PATENT DOCUMENTS

| | | |
|---|---|---|
| 3,631,122 A | 12/1971 | Berger |
| 3,751,504 A | 8/1973 | Keown et al. |
| 3,751,506 A | 8/1973 | Burress |
| 3,755,483 A | 8/1973 | Burress |
| 4,891,458 A | 1/1990 | Innes et al. |
| 4,992,606 A | 2/1991 | Kushnerick et al. |
| 5,105,041 A | 4/1992 | Ferk et al. |
| 5,149,894 A | 9/1992 | Holtermann et al. |
| 5,258,565 A | 11/1993 | Kresge et al. |
| 5,371,310 A | 12/1994 | Bennett et al. |
| 5,453,554 A | 9/1995 | Cheng et al. |
| 5,476,978 A | 12/1995 | Smith, Jr. et al. |
| 5,998,687 A | 12/1999 | Woodle et al. |
| 6,077,498 A | 6/2000 | Diaz Cabanas et al. |
| 6,252,126 B1 | 6/2001 | Netzer |

(Continued)

FOREIGN PATENT DOCUMENTS

| | | |
|---|---|---|
| EP | 0 432 814 | 6/1991 |
| EP | 0 629 549 | 12/1994 |

(Continued)

*Primary Examiner* — Thuan D Dang
(74) *Attorney, Agent, or Firm* — Roberts Mlotkowski Safran Cole & Calderon P.C.

(57) ABSTRACT

A process for producing an alkylated aromatic product in a reactor by reacting an alkylatable aromatic compound feedstock with another feedstock comprising alkene component and alkane component in a reaction zone containing an alkylation catalyst. The reaction zone is operated in predominantly liquid phase without inter-zone alkane removal. The polyalkylated aromatic compounds can be separated as feed stream for transalkylation reaction in a transalkylation reaction zone.

13 Claims, 2 Drawing Sheets

(56) References Cited

U.S. PATENT DOCUMENTS

| | | |
|---|---|---|
| 6,281,399 B1 * | 8/2001 | Schulz et al. ............. 585/323 |
| 6,995,295 B2 | 2/2006 | Clark et al. |
| 7,501,547 B2 | 3/2009 | Clark et al. |
| 2002/0128529 A1 | 9/2002 | Chen |
| 2004/0171899 A1 | 9/2004 | Pohl |

FOREIGN PATENT DOCUMENTS

| | | |
|---|---|---|
| EP | 0 949 227 | 10/1999 |
| WO | 97/17290 | 5/1997 |
| WO | 00/39253 | 7/2000 |
| WO | 01/21562 | 3/2001 |
| WO | 2004/026797 | 4/2004 |

* cited by examiner

ALKYLAROMATICS PRODUCTION USING DILUTE ALKENE

CROSS-REFERENCE TO RELATED APPLICATIONS

This application is a Continuation of U.S. Ser. No. 11/886,046, filed Mar. 17, 2008, now U.S. Pat. No. 7,923,589, which claims the benefit of 35 U.S.C. 371 National Stage Application of International Application No. PCT/US2006/007262, filed Mar. 1, 2006, which claims the benefit of Provisional Application No. 60/666,809, filed Mar. 31, 2005, the disclosures of which are hereby incorporated by reference in their entireties.

FIELD

The present invention relates to a process for producing alkylated aromatic products, particularly ethylbenzene and cumene.

BACKGROUND

Ethylbenzene is a key raw material in the production of styrene and is produced by the reaction of ethylene and benzene in the presence of an acid alkylation catalyst. Older ethylbenzene production plants, those typically built before 1980, used $AlCl_3$ or $BF_3$ as the acidic alkylation catalyst. Plants built after 1980 have in general used zeolite-based acidic catalysts as the alkylation catalyst.

Commercial ethylbenzene manufacturing processes typically require the use of concentrate ethylene that has a purity exceeding 80 mol. %. For example, a polymer grade ethylene has a purity exceeding 99 mol. % ethylene. However, the purification of ethylene streams to attain chemical or polymer grade is a costly process and hence there is considerable interest in developing processes that can operate with lower grade or dilute ethylene streams. One source of a dilute ethylene stream is the off gas from the fluid catalytic cracking or steam-cracking unit of a petroleum refinery. The dilute ethylene stream, after removal of reactive impurities, such as propylene, typically contains about 10-80 mol. % ethylene, with the remainder being ethane, hydrogen, methane, and/or benzene.

Three types of ethylation reactor systems are used for producing ethylbenzene, namely, vapor phase reactor systems, liquid phase reactor systems, and mixed phase reactor systems.

In vapor-phase reactor systems, the ethylation reaction of benzene and ethylene is carried out at a temperature of about 350 to 450° C. and a pressure of 690-3534 KPa-a (6-35 $kg/cm^2$-g) in multiple fixed beds of zeolite catalyst. Ethylene exothermically reacts with benzene to form ethylbenzene, although undesirable reactions also occur. About 15 mol. % of the ethylbenzene formed further reacts with ethylene to form di-ethylbenzene isomers (DEB), triethylbenzene isomers (TEB) and heavier aromatic products. All these undesirable reaction products are commonly referred as polyethylated benzenes (PEBs).

By way of example, vapor phase ethylation of benzene over the crystalline aluminosilicate zeolite ZSM-5 is disclosed in U.S. Pat. No. 3,751,504 (Keown et al.), U.S. Pat. No. 3,751,506 (Burress), and U.S. Pat. No. 3,755,483 (Burress).

In most cases, vapor phase ethylation systems use polymer grade ethylene feeds. Moreover, although commercial vapor phase processes employing dilute ethylene feeds have been built and are currently in operation, the investment costs associated with these processes is high.

In recent years the trend in industry has been to shift away from vapor phase reactors to liquid phase reactors. Liquid phase reactors operate at a temperature of about 150-280° C., which is below the critical temperature of benzene (290° C.). The rate of the ethylation reaction is lower compared with the vapor phase, but the lower design temperature of the liquid phase reaction usually economically compensates for the negatives associated with the higher catalyst volume.

Liquid phase ethylation of benzene using zeolite beta as the catalyst is disclosed in U.S. Pat. No. 4,891,458 and European Patent Publication Nos. 0432814 and 0629549. More recently it has been disclosed that MCM-22 and its structural analogues have utility in these alkylation/transalkylation reactions, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); International Patent Publication Nos. WO97/17290 and WO01/21562 (ITQ-2).

Commercial liquid phase ethylbenzene plants normally employ polymer grade ethylene. Moreover, although plants can be designed to accept ethylene streams containing up to 30 mol. % ethane by increasing the operating pressure, the costs associated with the design and operation of these plants have proven to be significant.

Technology has also been developed for the production of ethylbenzene in a mixed phase using reactive distillation. Such a process is described in U.S. Pat. No. 5,476,978. Mixed phase processes can be used with dilute ethylene streams since the reaction temperature of the ethylation reactor is below the dew point of the dilute ethylene/benzene mixture, but above the bubble point. The diluents of the ethylene feed, ethane, methane and hydrogen, remain essentially in the vapor phase. The benzene in the reactor is split between vapor phase and liquid phase, and the ethylbenzene and PEB reaction products remain essentially in the liquid phase.

U.S. Pat. No. 6,252,126 discloses a mixed phase process for producing ethylbenzene by reaction of a dilute ethylene stream containing 3 to 50 mol. % ethylene with a benzene stream containing 75 to 100 wt. % benzene. The reaction is conducted in an isothermal ethylation section of a reactor, which also includes a benzene stripping section, where the unreacted benzene is thermally stripped from the ethylation products. Integrated, countercurrent vapor and liquid traffic is maintained between the ethylation section and the benzene stripping section.

U.S. patent application Ser. No. 10/252,767 discloses a process for the production of ethylbenzene by reacting benzene with a dilute ethylene stream containing 20 to 80 wt. % ethylene and ethane. The reaction takes place in one of a series of series-connected reaction zones in the presence of an alkylation catalyst including a molecular sieve such as MCM-22. The temperature and pressure of the reaction zone being such that the benzene and dilute ethylene feedstock are under liquid phase conditions. The intermediate products between reaction zones are cooled and a portion of alkane, e.g., ethane, in the intermediate products is removed to maintain liquid phase by avoiding accumulation of ethane from zone to zone.

This invention relates a process for producing an alkylated aromatic compound in predominantly liquid phase alkylation reactor with an alkene feedstock containing alkene and at least 1 mol. % alkane without inter-zone alkane removal.

SUMMARY OF THE INVENTION

In one embodiment, this invention relates to a process for producing an alkylated aromatic compound in a reactor having a plurality of reaction zones including a first reaction zone and a second reaction zone, the process comprises the steps of:
(a) introducing a first feedstock and a second feedstock to the first reaction zone, wherein the first feedstock comprises an alkylatable aromatic compound(s), wherein the second feedstock comprises an alkene and at least 1 mol. % alkane;
(b) contacting the first feedstock and the second feedstock with a first catalyst in the first reaction zone to produce a first effluent, the first reaction zone being maintained under conditions such that the first reaction zone is predominately liquid phase, wherein the first effluent comprises an alkylated aromatic compound and alkane;
(c) cooling the first effluent without separation of the alkane from the first effluent;
(d) supplying at least a portion of the cooled first effluent and a third feedstock to the second reaction zone, wherein the third feedstock comprises an alkene; and
(e) contacting the at least a portion of the cooled first effluent and the third feedstock with a second catalyst in the second reaction zone to produce a second effluent, the second reaction zone being maintained under conditions such that the second reaction zone is predominately liquid phase.

In another embodiment, the process comprises another step of separating the first and second effluents to recover the alkylated aromatic compound. In yet another embodiment, the process comprises another step of separating at least a portion of liquid at the bottom of a reaction zone prior to the liquid exiting for cooling. In yet another embodiment, the process comprises another step of feeding at least a portion of vapor and/or liquid effluent at the bottom of a reaction zone prior to the liquid exiting for cooling to a downstream reaction zone.

In yet another embodiment, the process comprises a further step of contacting the first feedstock and the fourth feedstock with an alkylation catalyst in a by-passable pre-reactor upstream of the reactor, wherein the fourth feedstock comprises an alkene. In another embodiment, the process comprises a further step of contacting the second feedstock from the reactor under alkylation conditions with an alkylation catalyst in a finishing-reactor downstream of the reactor.

In one aspect of the above embodiment, the first and second catalysts is a molecular sieve selected from the group consisting of MCM-22, MCM-36, MCM-49, MCM-56, beta zeolite, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, or any combination thereof. In a preferred embodiment, the first and second catalysts have at least one catalyst composition. In an alternative embodiment, at least one reaction zone has a first catalyst composition and at least another reaction zone has a second catalyst composition.

In yet another aspect of any one of the above embodiments, the conditions in steps (b) and (e) include a temperature of 100 to 285° C. (212 to 500° F.) and a pressure of 689 to 4601 kPa-a (100 to 667 psia).

In another embodiment of this invention, the second, the third, and the fourth feedstocks comprise a mixture of first alkene component and a second alkene component. The first alkene component comprises 80 mol. % to 100 mol. % of the alkenes. The second alkene component comprises at least 10 mol. % alkene. Preferably, the second alkene component comprises from 20 to 80 mol. % alkene.

In one aspect of any one of the above embodiments, the second, the third, and the fourth feedstocks are made by 1) mixing the first alkene component and the second alkene component; and 2) adjusting the mixed component to the conditions of steps (b) and/or (e). In another aspect of any one of the above embodiments, the second feedstock is made by 1) adjusting the first alkene component and the second alkene component separately to the conditions of steps (b) or (e); and 2) mixing the conditioned first alkene component and the conditioned second alkene component.

In an alternative embodiment of this invention, the above mentioned processes are suitable for retrofitting an existing ethylbenzene or cumene plant with a vapor, liquid, or mixed phase alkylation reactor. In yet another embodiment of this invention, the above mentioned processes are suitable for retrofitting an existing $AlCl_3$ or $BF_3$ ethylbenzene or cumene plant.

In a preferred embodiment, the alkylated aromatic compound comprises ethylbenzene, the first feedstock comprises benzene, and the second, the third and the fourth feedstocks comprise a mixture of ethylene, methane, and ethane.

In another preferred embodiment, the alkylated aromatic compound comprises cumene, the first feedstock comprises benzene, and the second, the third and the fourth feedstocks comprise a mixture of propylene, propane, methane, and ethane.

In yet another preferred embodiment, this invention relates to a process for producing an alkylated aromatic compound in a reactor having a plurality of reaction zones including a first reaction zone and a second reaction zone, the process comprises the steps of:
(a) introducing a first feedstock and a second feedstock to the first reaction zone, wherein the first feedstock comprises an alkylatable aromatic compound(s), wherein the second feedstock comprises an alkene and at least 1 mol. % alkane;
(b) contacting the first feedstock and the second feedstock with a first catalyst in the first reaction zone to produce a first effluent, the first reaction zone being maintained under conditions such that the first reaction zone is predominately liquid phase, wherein the first effluent comprises an alkylated aromatic compound, alkane, and polyalkylated aromatic compound(s);
(c) cooling the first effluent without separation of the alkane from the first effluent;
(d) supplying at least a portion of the cooled first effluent and a third feedstock to the second reaction zone, wherein the third feedstock comprises an alkene;
(e) contacting the at least a portion of the cooled first effluent and the third feedstock with a second catalyst in the second reaction zone to produce a second effluent, the second zone being maintained under conditions such that the second reaction zone is predominately liquid phase, wherein the second effluent comprises the alkylated aromatic compound and the polyalkylated aromatic compound(s);
(f) separating at least a portion the first and/or second effluents to recover the polyalkylated aromatic compound(s) to form a transalkylation feed stream; and
(g) contacting at least a portion of the transalkylation feed stream with a fourth feedstock in the presence of a transalkylation catalyst to produce a transalkylation effluent under transalkylation conditions, wherein the fourth feedstock comprises an alkylatable aromatic compound(s), the transalkylation effluent which comprises the alkylated aromatic compound.

The above embodiment may further comprise the step of separating the transalkylation effluent to recover the alkylated aromatic compound.

In one aspect of the above embodiments, the transalkylation catalyst is a molecular sieve selected from the group consisting of MCM-22, MCM-36, MCM-49 and MCM-56, beta zeolite, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, or any combination thereof. In another aspect of the above embodiments, the transalkylation conditions of the transalkylation zone include temperature of 100 to 450° C. (212 to 842° F.) and a pressure of 689 to 4601 kPa-a (100 to 667 psia).

In one preferred embodiment, the alkylated aromatic compound comprises ethylbenzene. In another preferred embodiment, the alkylated aromatic compound comprises cumene.

DETAILED DESCRIPTION OF THE PREFERRED EMBODIMENTS

Detail Description of the Process

Figure 1:
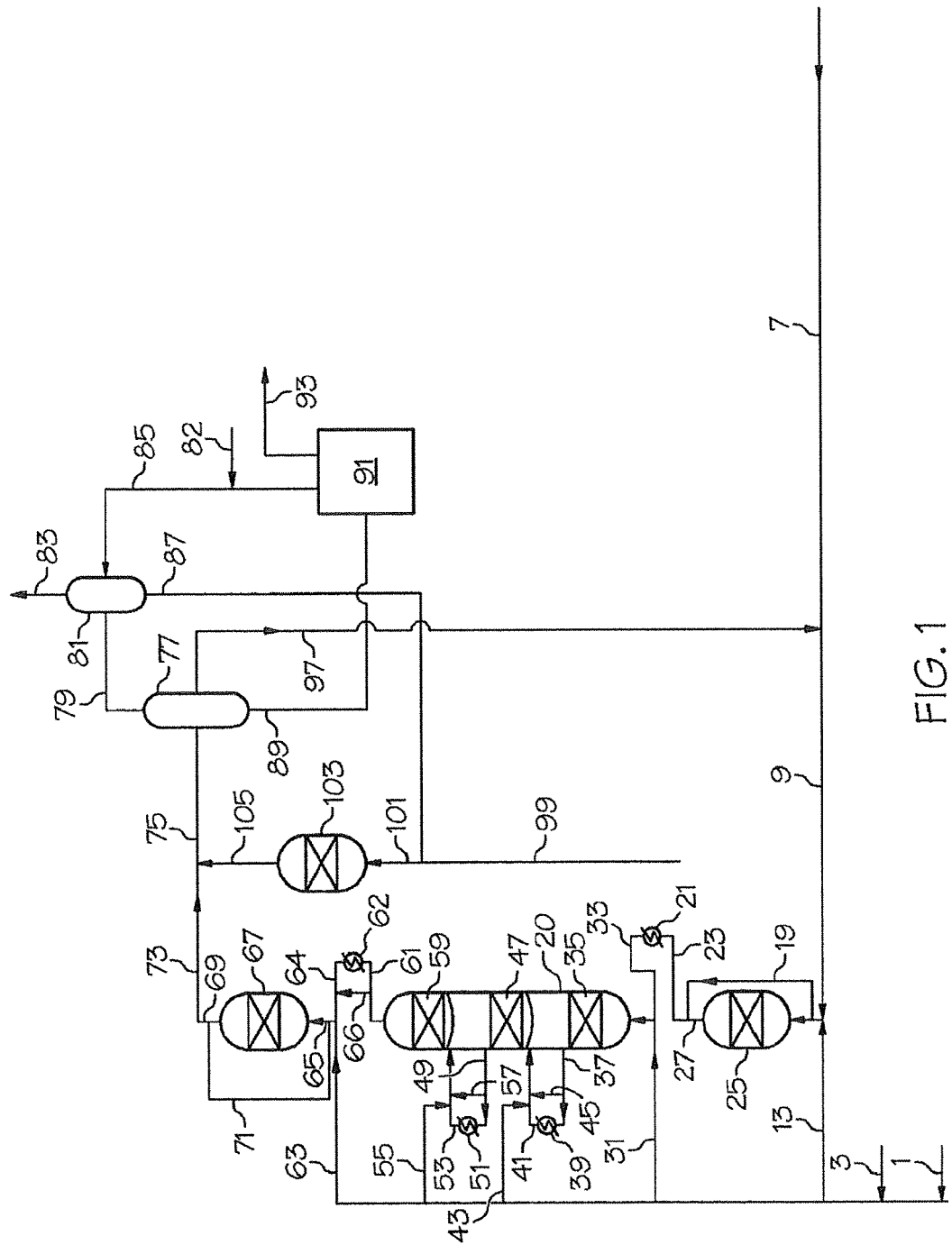
FIGS. 1 and 2 are flow diagrams of a process for producing ethylbenzene in accordance with the examples of the invention.

Referring to one embodiment of this invention as illustrated in FIG. 1, a reactor 20 has three reaction zones, a first reaction zone 35, a second reaction zone 47, and a third reaction zone 59. A first feedstock comprising an alkylatable aromatic compound, is fed to a by-passable reactive guard bed 25 via line 7 and further via line 9. A first alkene component comprising a concentrate alkene via line 1 is premixed with a second alkene component comprising dilute alkene via line 3 to form a second feedstock comprising an alkene and at least 1 mol. % alkane. The second feedstock is fed to the by-passable reactive guard bed 25 via line 13. A portion of both the first feedstock and the second feedstock may by-pass the reactive guard bed 25 via line 19. The reactive guard bed 25 may contain alkylation catalyst, e.g., MCM-22. The reactive guard bed 25 typically operates at or near 100% alkene conversion, but may operate at lower conversion so that the effluent of the reactive guard bed 25 leaving via line 27 is composed of alkylated aromatic compound (e.g., ethylbenzene or cumene), any unreacted alkene (e.g., ethylene), unreacted alkylatable aromatic compound (e.g., benzene), and unreacted light impurities (e.g., hydrogen, nitrogen, methane, and ethane). The reactive guard bed effluent in line 27 is further combined with the stream in line 19 and then passed to a heat exchanger 21 via line 23. An effluent of the heat exchanger 21 is fed to the reaction zone 35 via line 33. Additional second feedstock is fed to the reaction zone 35 via line 31. The conditions (temperature and pressure) of the reaction zone 35 is such that the mixed feedstocks is in predominantly liquid phase. The reaction zone 35 is packed with an alkylation catalyst, e.g., MCM-22. The unreacted alkylatable aromatic compound in the stream of line 33 is alkylated with the alkene in the additional second feedstock in line 31. An effluent from the reaction zone 35 is withdrawn from the reaction zone 35 via line 37. The conditions of the reaction zone 35 are such that the reaction zone 35 is maintained in predominantly liquid phase. The alkylation catalyst of the reaction zone 35 is typically operated at or near to 100% ethylene conversion.

An effluent from the reaction zone 35 is withdrawn from the reaction zone 35 via line 37, passed to a heat exchanger 39 prior to injection into the reaction zone 47 via line 41. A portion of the effluent from the reaction zone 35 may by-pass the heat exchanger 39 via line 45. Additional second feedstock is fed to the reaction zone 47 via line 43. The conditions of the reaction zone 47 are such that the reaction zone 47 is maintained in predominantly liquid phase. The alkylation catalyst of the reaction zone 47 is typically operated at or near to 100% ethylene conversion. An effluent from the reaction zone 47 is withdrawn from reaction zone 47 via line 49, passed to the heat exchanger 51 prior to injection in the reaction zone 59 via line 53. Again, a portion of the effluent from the reaction zone 47 may by-pass the heat exchanger 51 via line 57 and additional second feedstock is fed to reaction zone 59 via line 55. The conditions of the reaction zone 59 are such that the reaction zone 59 is maintained in predominantly liquid phase. The alkylation catalyst of the reaction zone 59 is typically operated at or near to 100% ethylene conversion. An effluent from the reaction zone 59 is withdrawn from reaction zone 59 via line 61, passed to the heat exchanger 62 prior to injection into a by-passable finishing-reactor 67 via line 64. Again, a portion of the effluent from the reaction zone 59 may by-pass the heat exchanger 62 via line 66 and additional second feedstock is fed to the by-passable finishing-reactor 67 via line 63. The conditions of the by-passable finishing-reactor 67 are such that the by-passable finishing-reactor 67 is maintained in predominantly liquid phase. A portion of the feed to the by-passable finishing-reactor 67 may by-pass the by-passable finishing-reactor 67 via line 71. The alkylation catalyst of the by-passable finishing-reactor 67 is typically operated at or near to 100% ethylene conversion.

The effluent of line 69 from the reaction zone 67 combining with the by-pass stream via line 71 leaves by-passable finishing-reactor 67 via line 73. The stream in line 73 containing the desired alkylated aromatic effluent as well as any unreacted alkene, unreacted alkylatable aromatic compound, polyalkylated aromatic compounds, methane, and ethane further via line 75 is fed to a separation block 77. The unreacted benzene is separated and withdrawn via line 97 recycling to the reaction zones. An overhead effluent of the separation block 77 containing benzene and lights (e.g., ethane, and methane), is withdrawn from separation block 77 via line 79 to a striper 81 where benzene is striped and withdrawn via line 87. The lights are removed via line 83. Heavies comprising the polyalkylated aromatic compounds separated from the separation block 77 are withdrawn from the separation block 77 via line 89 to a further separation block 91 where the polyalkylated aromatic compounds are separated and withdrawn via line 85 to the striper 81, optionally combined with additional polyalkylated aromatic compounds via line 82. The combined polyalkylated aromatic compounds strips the benzene component in the striper 81. A bottom stream of the striper 81 is withdrawn via line 87 further combines with additional first feedstock via line 99. The combined stream is fed to a transalkylation reactor 103 via line 101. The transalkylation reactors 103 is operated under conditions such that 20-100 wt. %, preferably 40 to 80 wt. %, of the polyalkylated aromatic compounds in the stream of line 101 are converted to alkylated aromatic compound. An effluent in line 105 from the transalkylation reactors is combined with the effluent of line 73 from the by-passable finishing reactor 67 as it passes to the separation block 77. The alkylated aromatic compound is separated as a effluent stream withdrawn via line 93.

Figure 2:
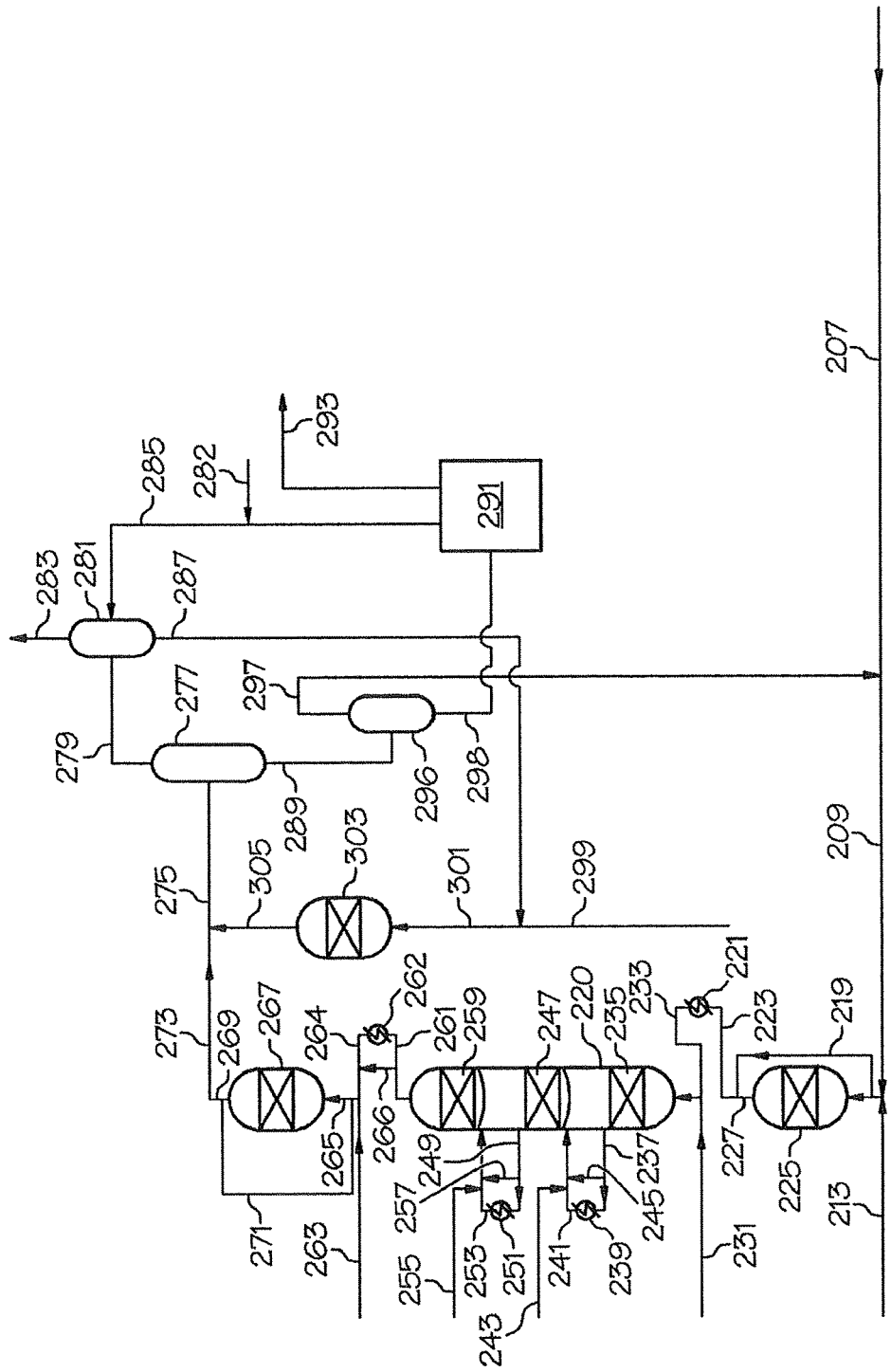

Referring to another embodiment of this invention as illustrated in FIG. 2, a reactor 221 has three reaction zones, a reaction zone 235, a reaction zone 247, and a reaction zone 259. A first feedstock comprising alkylatable aromatic compound is fed to a by-passable reactive guard bed 225 via line 207 and further via line 209. A second feedstock comprising alkene and at least 1 mol. % of alkane is fed to a reactive guard bed 225 via line 213. The second feedstock is a mixture of a first alkene component comprising a concentrate alkene and/or a second alkene component comprising dilute alkene. A portion of both the first feedstock and the second feedstock may by-pass the reactive guard bed 225 via line 219. The reactive guard bed 225 may contain alkylation catalyst, e.g., MCM-22. The reactive guard bed 225 typically operates at or near 100% alkene conversion, but may operate at lower conversion so that an effluent of line 227 leaving the reactive guard bed 225 is composed of alkylated aromatic compound (e.g., ethylbenzene or cumene), any unreacted alkene (e.g., ethylene), unreacted alkylatable aromatic compound (e.g., benzene), and unreacted light impurities (e.g., hydrogen, nitrogen, methane, and ethane). The reactive guard bed effluent in line 227 is further combined with the stream of line 219 and then passed to a heat exchanger 221 via line 223 before passing to the reaction zone 235 via line 233. Additional second feedstock is fed to the reaction zone 235 via line 231. The addition second feedstock is a mixture of a first alkene component comprising a concentrate ethylene and/or a second alkene component comprising dilute alkene, which may be different in composition from the second feedstock feeding through line 213. The conditions (temperature and pressure) of the reaction zone 235 is such that the mixed feedstocks is in predominantly liquid phase. The reaction zone 235 is packed with an alkylation catalyst, e.g., MCM-22. The unreacted alkylatable aromatic compound in feed of line 233 is alkylated with the alkene in the additional second feedstock via line 231. An effluent from the reaction zone 235 is withdrawn from the reaction zone 235 via line 237. The alkylation catalyst of the reaction zone 235 is typically operated at or near to 100% ethylene conversion.

The effluent from the reaction zone 235 is withdrawn from the reaction zone 235 via line 237, passed to a heat exchanger 239 prior to injection in the reaction zone 247 via line 241. A portion of the effluent from the reaction zone 235 may by-pass the heat exchanger 239 via line 245. Another additional second feedstock is fed to the reaction zone 247 via line 243. The conditions of the reaction zone 247 are such that the reaction zone 247 is maintained in predominantly liquid phase. The alkylation catalyst of the reaction zone 247 is typically operated at or near to 100% ethylene conversion. An effluent from the reaction zone 247 is withdrawn from reaction zone 247 via line 249, passed to a heat exchanger 251 prior to injection in the reaction zone 259 via line 253. Again, a portion of the effluent from the reaction zone 247 may by-pass the heat exchanger 251 via line 257 and additional second feedstock is fed to reaction zone 259 via line 255. The conditions of the reaction zone 259 are such that the reaction zone 259 is maintained in predominantly liquid phase. The alkylation catalyst of the reaction zone 259 is typically operated at or near to 100% ethylene conversion. An effluent from the reaction zone 259 is withdrawn from reaction zone 259 via line 261, passed to the heat exchanger 262 prior to injection in a by-passable finishing-reactor 267 via line 264. Again, a portion of the effluent from the reaction zone 259 may by-pass the heat exchanger 262 via line 266 and additional second feedstock is fed to the by-passable finishing-reactor 267 via line 263. The conditions of the by-passable finishing-reactor 267 are such that the by-passable finishing-reactor 267 is maintained in predominantly liquid phase. A portion of the feed to the by-passable finishing-reactor 267 may by-pass the by-passable finishing-reactor 267 via line 271. The alkylation catalyst of the by-passable finishing-reactor 267 is typically operated at or near to 100% ethylene conversion.

An effluent in line 269 from the reaction zone 269 combining with the by-pass stream via line 271 which contains the desired alkylated aromatic product as well as any unreacted alkene, unreacted alkylatable aromatic compound, polyalkylated aromatic compounds, methane, ethane. The combined stream is withdrawn via line 273 and further via line 290 feeding to a separation block 277. An overhead effluent of the separation block 277 containing benzene and lights (e.g., ethane, and methane), is withdrawn from separation block 277 via line 279 to a striper 281 where benzene is striped and withdrawn via line 287. The lights are removed via line 283. Heavies comprising the unreacted benzene and the polyalkylated aromatic compounds separated from the separation block 277 are withdrawn from the separation block 277 via line 289 to a separation block 296 where the unreacted benzene is separated as an overhead effluent and recycled via line 297. A bottom stream comprising polyalkylated aromatic compounds is withdrawn via line 298 to a further separation block 291. The polyalkylated aromatic compounds are separated and withdrawn via line 285 to a striper 281, optionally combined with additional polyalkylated aromatic compounds via line 282. The combined polyalkylated aromatic compounds strip the benzene component in the striper 281 and withdrawn via line 287 further combines with additional first feedstock via line 299. The combined stream is fed to a transalkylation reactor 303 via line 301. The transalkylation reactors 303 is operated under conditions such that 20-100 wt. %, preferably 40 to 80 wt. %, of the polyalkylated aromatic compounds are converted to alkylated aromatic compound. The effluent of line 305 from the transalkylation reactors is combined with the effluent of line 273 from the reactor 267 as it passes to the separation block 277. The alkylated aromatic compound is separated as a effluent stream withdrawn via line 293.

Feedstocks

The first feedstock comprises an alkylatable aromatic compound. The term "aromatic" in reference to the alkylatable compounds which are useful herein is to be understood in accordance with its art-recognized scope which includes alkyl substituted and unsubstituted mono- and polynuclear compounds. Compounds of an aromatic character, which possess a heteroatom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about C6 to about C12.

Reformate containing substantial quantities of benzene, toluene and/or xylene constitutes a particularly useful feed for the alkylation process of this invention. Although the process is particularly directed to the production of ethylbenzene from polymer grade and dilute ethylene, it is equally applicable to the production of other $C_7$-$C_{20}$ alkylaromatic compounds, such as cumene, as well as $C_6$+ alkylaromatics, such as $C_8$-$C_{16}$ linear and near linear alkylbenzenes.

The second feedstock comprises an alkene compound. Typically, the second feedstock includes a concentrated alkene feedstock (e.g., grade alkene) and a dilute alkene feedstock (e.g., catalytic cracking off-gas).

The concentrated alkene alkylating agent of the feedstock useful in the process of this invention includes an alkene feed comprised of at least 80 mol. % of the alkene and preferably at least 99 mol. % to 100 mol. %.

The dilute alkylating agent of the feedstock useful in the process of this invention includes a dilute alkene feed which contains at least one alkene and optionally at least one alkane. For example, where the alkene is ethylene, the alkane may be ethane and/or methane. Typically, the dilute alkene feed comprises at least 10 mol. % of the alkene, preferably from 20 to 80 mol. % of the alkene. One particularly useful feed is the dilute ethylene stream obtained as an off gas from the fluid catalytic cracking unit of a petroleum refinery.

In one embodiment of the invention, the second feedstock includes a concentrated alkene feedstock only. In another embodiment of the invention, the second feedstock includes a dilute alkene feedstock only. In yet another embodiment of the invention, the second feedstock is a mixture of a plurality of feedstocks having alkene and alkane e.g., at least one concentrated alkene feedstock having at least 80 mol. % alkene and at least one dilute alkene feedstock having 10-80 mol. % alkene.

In one embodiment, a plurality of feedstocks having alkene may be pre-mixed before being brought to the suitable conditions for alkylation reaction. In another embodiment of the invention, a plurality of feedstocks having alkene may be separately conditioned to the suitable conditions before feeding to the reaction zone(s). The relative amount of each separately conditioned alkene feedstock to be mixed and fed to the reaction zone(s) is varied based on the reaction conditions, catalyst (activity and amount), and space hour velocity. In one embodiment, the first few reaction zones of the reactor are fed with a second feedstock having higher alkene content than that of the second feedstock for the second few reaction zones.

Alkylation and Transalkylation Reactions

The alkylation reaction zone is operated in a predominantly liquid phase. In one embodiment, the inlet conditions of the inlet portion of the reaction zone include a temperature of 100 to 260° C. (212 to 500° F.) and a pressure of 689 to 4601 kPa-a (100 to 667 psia), preferably, a pressure of 1500 to 3500 kPa-a (218 to 508 psia). The conditions of the downstream reaction zone include a temperature of 150 to 285° C. (302 to 545° F.) and a pressure of 689 to 4601 kPa-a (100 to 667 psia), preferably, a pressure of 1500 to 3000 kPa-a (218 to 435 psia), a WHSV based on alkene for overall reactor of 0.1 to 10 $h^{-1}$, preferably, 0.2 to 2 $h^{-1}$, more preferably, 0.5 to 1 $h^{-1}$, or a WHSV based on both alkene and benzene for overall reactor of 10 to 100 $h^{-1}$, preferably, 20 to 50 $h^{-1}$. Typically temperature is higher in the downstream portion of the reaction zone than the inlet portion of the reaction zone due to the exothermic nature of the alkylation reaction. The alkylatable aromatic compound is alkylated with the alkene in the second feedstock in the presence of an alkylation catalyst in a reactor having at least two reaction zones. The reaction zones are typically located in a single reactor vessel, but may include a reaction zone including an alkylation catalyst bed, located in separate vessel which may be a by-passable and which may operate as a reactive guard bed. The catalyst composition used in the reactive guard bed may be different from the catalyst composition used in the alkylation reactor. The catalyst composition used in the reactive guard bed may have multiple catalyst compositions. At least the first alkylation reaction zone, and normally each alkylation reaction zone, is operated under conditions effective to cause alkylation of the alkylatable aromatic compound with the alkene component of the second feedstock in the presence of a alkylation catalyst.

The effluent from the first alkylation reaction zone (first product) comprises the desired alkylated aromatic product, unreacted alkylatable aromatic compound, any unreacted alkene (alkene conversion is expected to be at least 90 mol. %, preferably, about 98-99.9999 mol. %) and the alkane component and the other impurities. The temperature, pressure, and composition of the effluent is such that the effluent is maintained in predominantly liquid phase when the effluent exits the reaction zone. The temperature of the effluent is typically higher than the temperature of the feed because the alkylation reaction is generally exothermic. To maintain the next reaction zone in liquid-phase, the effluent is typically removed from the first reaction zone and cooled. The effluent can also be cooled by internal cooling system between reaction zones. The cooling step does not remove any unreacted alkane except to the extent of leak or loss due to equipment and operation. At least a portion of the effluent is fed to the second alkylation reaction zone where additional second feedstock is added for reaction with the unreacted alkylatable aromatic compound with a second catalyst. Where the process employs more than two alkylation reaction zones, the effluent from each zone is fed to the next zone with additional second feedstock. The effluent from the second reaction zone contains more unreacted alkane and more alkylated aromatic compound. Furthermore, at least a portion the effluent from the second alkylation reaction zone and/or other zones can be fed directly or indirectly to a transalkylation unit.

The term "predominately liquid phase" used herein is understood as having at least 95 wt. % liquid phase, preferably, 98 wt. %, more preferably, 99 wt. %, and most preferably, 99.5 wt. %.

In addition to, and upstream of, the alkylation zones, the alkylation reaction system may also include a by-passable reactive guard bed normally located in a pre-reactor separate from the remainder of the alkylation reactor. The reactive guard bed may also loaded with alkylation catalyst, which may be the same or different from the catalyst used in the multi-stage alkylation reaction system. The reactive guard bed is maintained from under ambient or up to alkylation conditions. At least a portion of alkylatable aromatic compound and typically at least a portion of the second feedstock are passed through the reactive guard bed prior to entry into the first reaction zone of the alkylation reaction zones in the reactor. The reactive guard bed not only serves to affect the desired alkylation reaction but is also used to remove any reactive impurities in the feeds, such as nitrogen compounds, which could otherwise poison the remainder of the alkylation catalyst. The catalyst in the reactive guard bed is therefore subject to more frequent regeneration and/or replacement than the remainder of the alkylation catalyst and hence the guard bed is normally provided with a by-pass circuit so that the alkylation feedstock can be fed directly to the series connected alkylation reaction zones in the reactor when the guard bed is out of service. The reactive guard bed operates in predominantly liquid phase and in co-current upflow or downflow operation.

The alkylation reactor used in the process of the present invention is normally operated so as to achieve essentially complete conversion of the alkene in the second feedstock. However, for some applications, it may be desirable to operate at below 100% alkene conversion. The employment a separate finishing reactor downstream of the multi-zones alkylation reactor may be desirable under certain conditions. The finishing reactor would also contain alkylation catalyst, which could be the same or different from the catalyst used in the alkylation reactor and could be operated under predominantly liquid phase alkylation conditions.

The alkylation reactor used in the process of the present invention is highly selective to the desired alkylated product, such as ethylbenzene, but normally produces at least some polyalkylated species. Thus the effluent from the final alkylation reaction zone is supplied to a transalkylation reactor which is normally separate from the alkylation reactor. The transalkylation reactor produces additional alkylated product by reacting the polyalkylated species with aromatic compound.

Particular conditions for carrying out the liquid phase alkylation of benzene with ethylene may a temperature of from about 120 to 285° C., preferably, a temperature of from about 150 to 260° C., a pressure of 689 to 4601 kPa-a (100 to 667 psia), preferably, a pressure of 1500 to 3000 kPa-a (218 to 435 psia), a WHSV based on ethylene for overall reactor of 0.1 to 10 $h^{-1}$, preferably, 0.2 to 2 $h^{-1}$, more preferably, 0.5 to 1 $h^{-1}$, or a WHSV based on both ethylene and benzene for overall reactor of 10 to 100 $h^{-1}$, preferably, 20 to 50 $h^{-1}$, and a mole ratio of benzene to ethylene from about 1 to about 10.

Particular conditions for carrying out the predominantly liquid phase alkylation of benzene with propylene may include a temperature of from about 80 to 160° C., a pressure of about 680 to about 4800 kPa-a; preferably from about 100 to 140° C. and pressure of about 2000 to 3000 kPa-a, a WHSV based on propylene of from about 0.1 about 10 $hr^{-1}$, and a mole ratio of benzene to ethylene from about 1 to about 10.

Where the alkylation system includes a reactive guard bed, it is operated under at least partial liquid phase conditions. The guard bed will preferably operate at a temperature of from about 120 to 285° C., preferably, a temperature of from about 150 to 260° C., a pressure of 689 to 4601 kPa-a (100 to 667 psia), preferably, a pressure of 1500 to 3000 kPa-a (218 to 435 psia), a WHSV based on ethylene for overall reactor of 0.1 to 10 $h^{-1}$, preferably, 0.2 to 2 $h^{-1}$, more preferably, 0.5 to 1 $h^{-1}$, or a WHSV based on both ethylene and benzene for overall reactor of 10 to 100 $h^{-1}$, preferably, 20 to 50 $h^{-1}$, and a mole ratio of benzene to ethylene from about 1 to about 10.

The polyalkylated aromatic compounds in the effluents may be separated for transalkylation with alkylatable aromatic compound(s). The alkylated aromatic compound is made by transalkylation between polyalkylated aromatic compounds and the alkylatable aromatic compound.

The transalkylation reaction takes place under predominantly liquid phase conditions. Particular conditions for carrying out the predominantly liquid phase transalkylation of polyethylbenzene(s) with benzene may include a temperature of from about 150° to about 260° C., a pressure of 696 to 4137 kPa-a (101 to 600 psia), a WHSV based on the weight of the polyethylbenzene(s) feed to the reaction zone of from about 0.5 to about 100 $hr^{-1}$ and a mole ratio of benzene to polyethylbenzene(s) of from 1:1 to 30:1, preferably, 1:1 to 10:1, more preferably, 1:1 to 5:1.

In another embodiment, the transalkylation reaction takes place under vapor phase conditions. Particular conditions for carrying out the vapor phase transalkylation of polyethylbenzenes with benzene may include a temperature of from about 350 to about 450° C., a pressure of 696 to 1601 kPa-a (101 to 232 psia), a WHSV based on the weight of the polyethylbenzene(s) feed to the reaction zone of from about 0.5 to about 20 $hr^{-1}$, preferably, from about 1 to about 10 $hr^{-1}$, and a mole ratio of benzene to polyethylbenzene(s) of from 1:1 to 5:1, preferably, 2:1 to 3:1.

In an alternative embodiment of this invention, the above mentioned processes are suitable for retrofitting an existing ethylbenzene or cumene plant with a vapor, liquid, or mixed phase alkylation reactor. In particular, the process of this invention may be used to retrofit an existing ethylbenzene or cumene plant using polymer grade or chemical grade ethylene or propylene with minimum amount of new equipments, such as, extra compressors for the second feedstock, extra-separation column for light gas and aromatics, and other equipment.

Catalysts

The alkylation and transalkylation catalyst used in the process of the invention is not critical but normally comprises at least one of MCM-22, MCM-49, MCM-36, MCM-56, beta zeolite, faujasite, mordenite, PSH-3, SSZ-25, ERB-1, ITQ-1, ITQ-2 and optionally SAPO molecular sieves (e.g., SAPO-34 and SAPO-41).

MCM-22 and its use to catalyze the synthesis of alkylaromatics, including ethylbenzene, is described in U.S. Pat. Nos. 4,992,606; 5,077,445; and 5,334,795. PSH-3 is described in U.S. Pat. No. 4,439,409. SSZ-25 and its use in aromatics alkylation are described in U.S. Pat. No. 5,149, 894. ERB-1 is described in European Patent No. 0293032. ITQ-1 is described in U.S. Pat. No. 6,077,498. ITQ-2 is described in International Patent Publication No. WO97/17290 and WO01/21562. MCM-36 is described in U.S. Pat. Nos. 5,250,277 and 5,292,698. U.S. Pat. No. 5,258,565 describes the synthesis of alkylaromatics, including ethylbenzene, using a catalyst comprising MCM-36. MCM-49 is described in U.S. Pat. No. 5,236,575. The use of MCM-49 to catalyze the synthesis of alkylaromatics, including ethylbenzene, is described in U.S. Pat. Nos. 5,508,065 and 5,371,310. MCM-56 is described in U.S. Pat. No. 5,362,697. The use of MCM-56 to catalyze the synthesis of alkylaromatics including ethylbenzene is described in U.S. Pat. Nos. 5,557,024 and 5,453,554. The entire contents of all the above patent specifications are incorporated herein by reference.

Alternatively, the alkylation and transalkylation catalyst can comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5 is described in detail in U.S. Pat. No. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

As a further alternative, the alkylation and transalkylation catalyst can comprise a large pore molecular sieve having a Constraint Index less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The same catalyst may be used in both the transalkylation zone and the alkylation zones of the present invention. Preferably, however, catalysts are chosen for the different alkylation zones and the transalkylation zone, so as to be tailored for the particular reactions catalyzed therein. In one embodiment of the present invention, a standard activity catalyst for example, 50% zeolite and 50% binder is used in the higher temperature alkylation catalyst beds and a higher activity catalyst for example, 75% zeolite and 25% binder is used in the lower temperature alkylation catalyst beds, while suitable transalkylation catalyst is used in the transalkylation zone. In such an embodiment, any finishing reactor zone could include a MCM-22 catalyst bed for predominantly liquid phase operation.

In the process of the invention, the alkylation reaction in at least the first, and normally in each, of the alkylation reaction zones takes place under predominantly liquid phase conditions, such that the alkylatable aromatic compound is in the predominantly liquid phase.

The invention will be more particularly described with reference to the following Examples.

EXAMPLES

Example 1

Liquid Phase Alkylation

The following example is a computer simulation of benzene ethylation with ethylene in liquid phase. Simulation results were obtained using a proprietary numerical software package. Vapor-liquid equilibrium was calculated, the Soave-Redlich-Kwong Equation-of-State (with optimized interaction coefficients).

The feed to each catalyst bed is characterized by a B/E ratio (Benzene to Ethylene molar ratio) and an E/E ratio (Ethylene to Ethane molar ratio). The very high E/E ratio is an indication of an ethylene feedstock with a polymer grade ethylene purity. This case is configured to operate in the liquid phase with high E/E ratio. The temperatures and pressures of the feed and effluent streams to each bed are sufficient to allow all liquid phase operation in the catalyst bed. The results of the simulation are shown in Table 1.

TABLE 1

|  |  | Ethylene conversion (%) | EB cumulative yield (mol. %) | B/E ratio | E/E ratio | Fraction Liquid | T (° C.) | P (kPa-a) |
|---|---|---|---|---|---|---|---|---|
| Bed 1 | Feed | — | — | 21.0 | 261 | 1 | 222.2 | 4270 |
|  | Effluent | 100 | 4.8 | — | — | 1 | 246.3 | 4220 |
| Bed 2 | Feed | — | — | 20.0 | 229 | 1 | 242.6 | 4210 |
|  | Effluent | 100 | 9.0 | — | — | 1 | 265 | 4165 |
| Bed 3 | Feed | — | — | 19.1 | 218 | 1 | 222.9 | 4035 |
|  | Effluent | 100 | 13.0 | — | — | 1 | 246.4 | 3980 |
| Bed 4 | Feed | — | — | 18.1 | 183 | 1 | 242.9 | 3980 |
|  | Effluent | 100 | 16.9 | — | — | 1 | 264.9 | 3915 |
| Bed 5 | Feed | — | — | 17.2 | 166 | 1 | 223.5 | 3715 |
|  | Effluent | 100 | 20.6 | — | — | 1 | 246.4 | 3660 |
| Bed 6 | Feed | — | — | 16.3 | 152 | 1 | 243.1 | 3660 |
|  | Effluent | 100 | 24.1 | — | — | 1 | 264.7 | 3590 |

Example 2

Liquid Phase Alkylation with Mixed Ethylene Feedstocks

The following example is a computer simulation of mixed-phase/liquid-phase benzene ethylation with mixed ethylene feedstocks by the process of the present invention. The case is configured to operate in liquid-phase. The temperatures and pressures of the feed and effluent streams to each bed are sufficient to allow liquid-phase operation in the catalyst bed. The results of the simulation are shown in Table 2.

Option 1 for modification of the plant after addition of dilute ethylene has the characteristics shown in Table 2. The feed to each catalyst bed is characterized by a B/E ratio (Benzene to Ethylene molar ratio) and an E/E ratio (Ethylene to Ethane molar ratio). The E/E ratio is significantly lower than in the base-case (example 1) indicating a greater concentration of ethane and representative of dilute ethylene streams and/or mixed chemical/polymer grade and dilute ethylene streams. The entire contents of this dilute ethylene configuration operates in the liquid phase (after sufficient residence time is allowed downstream of the ethylene/ethane injectors to allow the ethylene/ethane to completely dissolve in the liquid. The Temperatures and Pressures of the feed and effluent streams to each bed are sufficient to allow all liquid phase operation in the catalyst bed.

The E/E ratio decreases from bed to bed in the reactor because while the ethylene is consumed, the ethane builds up in the reactor. In addition, the average temperature of each pair of catalyst beds decreases down the length of the reactor to compensate for the ethane build-up and reduced pressure, due to pressure drop across the catalyst beds. In this way, a total liquid phase is maintained even in the presence of significant amounts of ethane, which, if maintained at base-case conditions, would cause the reaction mixture to be in a mixed-phase (liquid/vapor) state.

Example 3

Liquid Phase Alkylation with Mixed Ethylene Feedstocks

Option 2 for modification of the plant after addition of dilute ethylene has the characteristics shown in Table 3. The feed to each catalyst bed is characterized by a B/E ratio (Benzene to Ethylene molar ratio) and an E/E ratio (Ethylene to Ethane molar ratio). The E/E ratio is significantly lower than in the base-case (example 1) indicating a greater concentration of ethane and representative of dilute ethylene streams and/or mixed chemical/polymer grade and dilute ethylene streams. The entire contents of this dilute ethylene configuration operates in the liquid phase (after sufficient residence time is allowed downstream of the ethylene/ethane injectors to allow the ethylene/ethane to completely dissolve in the liquid. The Temperatures and Pressures of the feed and effluent streams to each bed are sufficient to allow all liquid phase operation in the catalyst bed.

Similarly to example 2, the E/E ratio decreases from bed to bed in the reactor because while the ethylene is consumed, the ethane builds up in the reactor. In addition, the average temperature of each pair of catalyst beds decreases down the length of the reactor to compensate for the ethane build-up and reduced pressure, due to pressure drop across the catalyst beds. In this way, a total liquid phase is maintained even in the presence of significant amounts of ethane, which, if maintained at base-case conditions, would cause the reaction mixture to be in a mixed-phase (liquid/vapor) state.

Dissimilar to example 2, the E/E ratio of the beds nearest the inlet is significantly larger than the E/E ratio of those same beds in example 2. This indicates that more chemical/polymer grade ethylene is introduced in the inlet beds and more dilute ethylene feed is introduced in the outlet beds. Consistent with this, the temperature of beds 2 & 4 in particular are much higher than the temperature of these same beds in example 2. Catalyst beds 1 & 2 tend to be close in temperature in both example 2 and example 3 because the total amount of C2 (ethylene and ethane).

TABLE 2

| | | Ethylene conversion (%) | EB cumulative yield (%) | B/E ratio | E/E ratio | Fraction Liquid | T (° C.) | P (kPa-a) |
|---|---|---|---|---|---|---|---|---|
| Bed 1 | Feed | | | 15.9 | 4.5 | 1 | 225.7 | 4270 |
| | Effluent | 100 | 6 | | | 1 | 256.3 | 4220 |
| Bed 2 | Feed | | | 36.5 | 3.2 | 1 | 253.2 | 4210 |
| | Effluent | 100 | 8.2 | | | 1 | 264.8 | 4165 |
| Bed 3 | Feed | | | 13.6 | 2.1 | 1 | 179.9 | 3925 |
| | Effluent | 100 | 13.5 | | | 1 | 214.9 | 3870 |
| Bed 4 | Feed | | | 17.0 | 1.2 | 1 | 211.8 | 3870 |
| | Effluent | 100 | 17.2 | | | 1 | 235.8 | 3805 |
| Bed 5 | Feed | | | 14.5 | 1.0 | 1 | 180.4 | 3635 |
| | Effluent | 100 | 21 | | | 1 | 208.1 | 100 |
| Bed 6 | Feed | | | 31.2 | 0.42 | 1 | 206.9 | 3580 |
| | Effluent | 100 | 22.5 | | | 1 | 218.5 | 3510 |

TABLE 3

|  |  | Ethylene conversion (%) | EB cumulative yield (%) | B/E ratio | E/E ratio | Fraction Liquid | T (° C.) | P (kPa-a) |
|---|---|---|---|---|---|---|---|---|
| Bed 1 | Feed |  |  | 15.1 | 15.0 | 1 | 214.2 | 4320 |
|  | Effluent | 100 | 6.4 |  |  | 1 | 247.7 | 4270 |
| Bed 2 | Feed |  |  | 20.9 | 6.7 | 1 | 243.8 | 4210 |
|  | Effluent | 100 | 10.2 |  |  | 1 | 264.7 | 4165 |
| Bed 3 | Feed |  |  | 14.6 | 6.4 | 1 | 222 | 4035 |
|  | Effluent | 100 | 15.2 |  |  | 1 | 251.6 | 3980 |
| Bed 4 | Feed |  |  | 21.0 | 3.5 | 1 | 248.3 | 3980 |
|  | Effluent | 100 | 18.3 |  |  | 1 | 266.3 | 3915 |
| Bed 5 | Feed |  |  | 14.4 | 1.2 | 1 | 179.6 | 3685 |
|  | Effluent | 100 | 21.5 |  |  | 1 | 207.3 | 3630 |
| Bed 6 | Feed |  |  | 41.9 | 0.31 | 1 | 206 | 3630 |
|  | Effluent | 100 | 22.5 |  |  | 1 | 214.5 | 3560 |

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for producing an alkylated aromatic compound in a reactor having a plurality of reaction zones including a first reaction zone and a second reaction zone, said process comprising the steps of:
(a) introducing a first feedstock and a second feedstock to said first reaction zone, wherein said first feedstock comprises an alkylatable aromatic compound, wherein said second feedstock comprises an alkene and at least 1 wt. % alkane, said first reaction zone maintained under conditions such that said first reaction zone is predominately liquid phase having at least 95 wt. % liquid phase;
(b) contacting said first feedstock and said second feedstock with a first catalyst in said first reaction zone to produce a first effluent, wherein at least 90 mole percent the alkene present in said first feedstock is converted and said first effluent comprises an alkylated aromatic compound and alkane;
(c) cooling said first effluent through a heat exchanger without separation of said alkane from said first effluent;
(d) supplying at least a portion of said cooled first effluent and a third feedstock to said second reaction zone, wherein said third feedstock has the same composition as said second feedstock, said second reaction zone maintained under conditions such that said second reaction zone is predominately liquid phase having at least 95 wt. % liquid phase; and
(e) contacting said at least a portion of said cooled first effluent and said third feedstock with a second catalyst in said second reaction zone to produce a second effluent;
wherein said second reaction zone is operated to achieve essentially complete conversion of the alkene, wherein said alkylated aromatic compound comprises ethylbenzene, said alkylatable aromatic compound of said first feedstock consists of benzene and optionally ethylbenzene and cumene, and said second feedstock and said third feedstock comprise a mixture of ethylene and ethane.

2. The process of claim 1, wherein said first and second catalysts are a molecular sieve selected from the group consisting of MCM-22, MCM-36, MCM-49 and MCM-56, beta zeolite, faujasite, mordenite, PSH-3, SSZ-25, ERB-I, ITQ-I, ITQ-2, zeolite Y, Ultrastable Y (USY), Dealuminized Y, rare earth exchanged Y (REY), ZSM-3, ZSM-4, ZSM-I8, ZSM-20, or any combination thereof.

3. The process of claim 1, wherein said conditions in steps (b) and (e) include a temperature of 120 to 285° C. and a pressure of 689 to 4601 kPa-a (100 to 667 psia), a WHSV based on the weight of alkene of 0.1 to 10 $h^{-1}$.

4. The process of claim 1, wherein said second feedstock comprises ethylene and a second alkene component, and said third feedstock comprises ethylene and a second alkene component.

5. The process of claim 4, wherein said second alkene component comprises at least 20 mol. % alkene.

6. The process of claim 4, wherein said second alkene component comprises from 20 to 80 mol. % alkene.

7. The process of claim 1, further comprising the step of:
(f) separating said second effluent to recover said alkylated aromatic compound.

8. The process of claim 1, further comprising the step of contacting said first feedstock and a fourth feedstock with an alkylation catalyst in a by-passable pre-reactor upstream of said reactor, wherein said fourth feedstock comprises an alkene.

9. The process of claim 1, further comprising the step of contacting said second effluent under alkylation conditions with an alkylation catalyst in a finishing-reactor downstream of said reactor.

10. The process of claim 1, wherein said second effluent comprises ethylbenzene and polyalkylated aromatic compounds and said process further comprises;
(a) separating at least a portion said first and/or second effluents to recover said polyalkylated aromatic compound(s) to form a transalkylation feed stream; and (b) contacting at least a portion of said transalkylation feed stream with a fourth feedstock in the presence of a transalkylation catalyst to produce a transalkylation effluent under transalkylation conditions, wherein said fourth feedstock comprises an alkylatable aromatic compound(s), said transalkylation effluent which comprises ethylbenzene.

11. The process of claim 10, further comprising the step of:

(c) separating said transalkylation effluent to recover ethylbenzene.

12. The process of claim 10, wherein said transalkylation catalyst is a molecular sieve selected from the group consisting of MCM-22, MCM-36, MCM-49 and MCM-56, beta zeolite, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, or any combination thereof.

13. The process of claim 10, wherein said transalkylation conditions include a temperature of 150 to 260° C. and a pressure of 696 to 4137 kPa-a (101 to 600 psia), a WHSV based on the weight of said polyalkylated aromatic compounds of about 0.5 to 100 $h^{-1}$, a mole ratio of ethylbenzene to said polyalkylated aromatic compounds of 1:1 to 10:1.

* * * * *